(12) United States Patent
Bianchi et al.

(10) Patent No.: US 6,589,998 B1
(45) Date of Patent: Jul. 8, 2003

(54) GEL COMPOSITION FOR FILLING A BREAST MILK DUCT PRIOR TO SURGICAL EXCISION OF THE DUCT OR OTHER BREAST TISSUE

(75) Inventors: Annette Bianchi, San Mateo, CA (US); Julian Nikolchev, Portola Valley, CA (US); David Hung, Belmont, CA (US); Eyal Ron, Lexington, MA (US); Linda Gont, Cedarburg, WI (US); Susan Love, Pacific Palisades, CA (US); Tina Patel, San Carlos, CA (US)

(73) Assignee: Cytyc Health Corporation, Boxborough, MA (US)

( * ) Notice: Subject to any disclaimer, the term of this patent is extended or adjusted under 35 U.S.C. 154(b) by 0 days.

(21) Appl. No.: 09/590,517

(22) Filed: Jun. 9, 2000

Related U.S. Application Data

(60) Provisional application No. 60/138,693, filed on Jun. 11, 1999.

(51) Int. Cl.$^7$ .................. A61K 47/32; A61K 31/74; A61K 9/14; A61F 13/00
(52) U.S. Cl. .................. 514/772.4; 514/944; 424/78.02; 424/422; 424/484; 424/486
(58) Field of Search ............................. 514/772.4, 944; 424/9, 78.02, 422, 484, 486

(56) References Cited

U.S. PATENT DOCUMENTS

| | | | |
|---|---|---|---|
| 4,188,373 A | * | 2/1980 | Krezanoski ............. 424/78 |
| 4,619,913 A | | 10/1986 | Luck et al. |
| 5,475,052 A | | 12/1995 | Rhee et al. |
| 5,587,175 A | | 12/1996 | Viegas et al. |
| 5,607,477 A | | 3/1997 | Schindler et al. |
| 5,626,863 A | | 5/1997 | Hubbel et al. |
| 5,660,854 A | | 8/1997 | Haynes et al. |
| 5,707,647 A | | 1/1998 | Dunn et al. |
| 5,709,854 A | | 1/1998 | Griffith-Cima et al. |
| 5,716,404 A | | 2/1998 | Vacanti et al. |
| 5,717,030 A | | 2/1998 | Dunn et al. |
| RE35,748 E | | 3/1998 | Luck et al. |
| 5,733,950 A | | 3/1998 | Dunn et al. |
| 5,776,093 A | | 7/1998 | Goldenberg |
| 5,776,094 A | | 7/1998 | Goldenberg |
| 5,776,095 A | | 7/1998 | Goldenberg |
| 5,780,044 A | | 7/1998 | Yewey et al. |
| 5,792,469 A | | 8/1998 | Tipton et al. |
| 5,856,367 A | | 1/1999 | Barrows et al. |
| 5,861,174 A | | 1/1999 | Stratton et al. |
| 6,287,707 B1 | * | 9/2001 | Luthra et al. ............. 428/522 |

FOREIGN PATENT DOCUMENTS

| | | |
|---|---|---|
| JP | 6221171 | * 10/1987 |
| WO | WO 96/02276 | 2/1996 |
| WO | WO 96/11671 | 4/1996 |
| WO | WO 96/31547 | 10/1996 |
| WO | WO 97/00275 | 1/1997 |
| WO | WO 97/05185 | 2/1997 |
| WO | WO 97/15242 | 5/1997 |
| WO | WO 97/22371 | 6/1997 |

OTHER PUBLICATIONS

Baker et al, "Ductal abnormalities detected with galactography: frequency of adequate excisional biopsy," AJR Am J. Roentgenol. 1994; 162(4):821–4.

Bjorn–Hansen "Contrast mammography," British J Radiol, 38, pp 947–951, Dec. 1965.

Caiatto, et al, Tumori 1988 74(2):177–81.

Cardenosa et al. "Ductography of the breast: technique and findings," Am J. Roentgenol 1994 May: 162(5):1081–7.

Choudhury et al. "A New surgical localization technique for biopsy in patients with nipple discharge," Arch Surg 1989 Jul.: 124(7), 874–5.

Grillo et al. "Chromogactography preceding ductal–lobular unit excision for nipple discharge," Annales Chiurgiae et Gynaecologiae 79:6–9 1990.

Hou et al. "A simple method of duct cannulation and localization for galactography before excision in patients with nipple discharge" Radiology, (May 1995) 195 (2) 568–9.

Hou, et al, "Evaluation of galactography for nipple discharge" Clin Imaging 1998 22(2):89–94.

Karesen et al. "Microductectomy. A simple method for excision of intraductal changes in the breast," Tidsskr Nor Laegeforen 1993 Apr. 20:113(10):1233–5 (English abstract only of Norwegian article).

Moffat & Going, "Three dimensional anatomy of complete duct systems in human breast: pathologal and developemental implicatins," J Clin Path 1996:49:48–52.

Ohtake et al. "Intraductal extension of primary invasive breast carcinoma treated by breast conservative surgery," Cancer Jul. 1, 1995 vol. 76, No. 1.

Okazaki et al. "Diagnosis of nonpalpable breast cancer by ductoscopy: comparison of imaging and histological findings," Nyugan no Rinsho[clinical breast cancer] 4(4):587–594(Dec. 1989).

Okazaki et al. "Progress of ductoscopy of the breast," Nippon Geka Gakkai Zasshi May 1996: 97 (5):357–62 (English abstract only of Japanese article).

Osborne "Galactography with contrast and dye," Australian Radialogy vol. 23, No. 3 8/89.

(List continued on next page.)

*Primary Examiner*—Thurman K. Page
*Assistant Examiner*—Blessing Fubara
(74) *Attorney, Agent, or Firm*—Banner & Witcoff, Ltd.

(57) ABSTRACT

The invention is a gel composition for delivery to a breast milk duct prior to surgical excision of breast tissue including cancerous lesions. The invention also provides methods of mapping all or nearly all of a breast milk duct prior to surgical excision of breast tissue, and method of identifying part or all of a breast duct or ducts as a surgical aide to a breast surgeon. Kits to support these methods and including these compositions are also provided.

10 Claims, No Drawings

OTHER PUBLICATIONS

Pansera, "Accessibility and possibility of elimination of breast epithelium: the theoretical possibility of preventing breast carcinoma through destruction of the epithelium of originin," Medical Hypotheses 33 107–111 (1990).

Papanicolaou et al. "Exfoliative cytology of the human mammary gland and its value in the diagnosis of cancer and other diseases of the breast," Cancer Mar.–Apr. 1958, 11(2):377–409.

Sartorius et al. "Contrast ductography for the recognition and localization of benign and malignant breast lesions: an improved technique," *Breast Cancer* New York Wiley pp281–300, 1977.

Sartorius "Fluid Cytology and contrast Ductography".

Stanec et al. "Microdochectomy with perioperative dye localization of ducts in patients with nipple secretions," Lijec Vjesn 1993 Jan.–Feb.: 115(1–2):17–20 (English abstract only of Serbo–Croation article).

Tabar et al. "Galactography: the diagnostic procedure of choice for nipple discharge," Radiology 149:31–38 Oct. 1983.

Trott et al, "Cyanocrylate tissue adhesives" JAMA 1997 May 21; 277(19):1559–1560.

Van Zee et al. "Preoperative galactography increases the diagnostic yield of major duct excision for nipple discharge," Cancer 1998; 82(10): 1874–80.

* cited by examiner

GEL COMPOSITION FOR FILLING A BREAST MILK DUCT PRIOR TO SURGICAL EXCISION OF THE DUCT OR OTHER BREAST TISSUE

CROSS-REFERENCES TO RELATED APPLICATIONS

This application claims the benefit of the following provisional application under 37 CFR §1.78: U.S. Provisional Application No. 60/138,693 filed Jun. 11, 1999. The full disclosure of this application is incorporated herein by reference.

BACKGROUND OF THE INVENTION

1. Field of the Invention

The field of this invention is gel compositions for delivery to a breast milk duct for mapping a duct or ducts before surgical excision of any part of the breast or ductal system.

2. Description of the Background Art

Breast cancer is the most common cancer in women, with well over 100,000 new cases being diagnosed each year (see e.g. Goodson W H & King E B, Chapter 4: Discharges and Secretions of the Nipple, The Breast: Comprehensive Management of Benign and Malignant Diseases 2nd Ed. vol 2, Bland & Kirby eds. W. B. Saunders Co, Philadelphia, Pa. pp. 51–74, (1998)). Breast cancer usually arises from a single ductal system and exists in a precancerous state for a number of years. Surgical procedures can include removal of part or all of a duct containing a cancerous lesion (a ductectomy), removal of a lump in a breast duct (a lumpectomy), or performing a partial or total mastectomy. These procedures would be well served with surgical adjuvants to aid the practitioner to identify the duct or ducts or part of the duct to be removed. For a complete description of such procedures on the breast, and definitions of the various types of breast tissue removal procedures, see Love, S. THE BREAST BOOK, $2^{nd}$ Ed. Lindsey Ed. Perseus Books, Reading Mass. 1995.

Lumpectomies, ductectomies (partial or complete) and mastectomies (partial or complete) are successful only to the extent that all cancerous tissue is removed during the surgical procedure. Since breast cancer originates in a breast duct or ducts, identifying the duct or ducts affected for surgery can provide a surgeon with a well needed, previously unavailable tool with which to generate clean margins at the excision, increase the likelihood of getting all the cancer with the excision, and increase long term likelihood of success from the procedure. The present invention provides such benefits to breast cancer patients and practitioners in the field.

3. Relevant Literature

Preoperative galactography (the injection of liquid dye into breast ducts) has been used to target a lesion in a breast duct before surgical excision of the breast duct, as described in Van Zee et al., Cancer 1998 82:1874–80, Hou et al., Clin Imaging 1998 22:89–94, Vega et al., Acta Radiologica 1997 38:240–2, Hou et al., Radiology 1995 195:568–9, Baker et al., AJR Am J Reontgenol 1994 162:821–4, and Grillo et al., AnnChir Bynaecol 1990 79:6–9.

A process for forming an ablative or protective corneal shield or mask using an in situ forming gel applied to the eye are described and claimed in U.S. Pat. No. 5,587,175 to MDV Technologies for use in ophthalmic laser surgery and drug delivery to the eye.

Biodegradable in situ forming implants and methods of producing them are described in U.S. Pat. No. 5,733,950 to Atrix Pharmaceuticals using a water insoluble biodegradable polymer dissolved in a water soluble organic solvent for the purpose of drug delivery to a site in the body including the mouth, periodontal pocket, the eye or the vagina where there is considerable fluid flow.

SUMMARY OF THE INVENTION

The invention provides a biocompatable composition comprising a polymer that has a solubility greater than 0.5 grams per 100 ml of solvent, a molecular weight in a range of between about 1 and 500 kilodaltons and a weight/weight ratio of polymer to solvent in a range between about 0.5:100 to 100:0.5; the composition is liquid in a solvent and undergoes a gel transition inside a target breast milk duct within about 30 minutes of delivery of the composition to the target duct. The gel transition time can be in a range from about 0 to 2 minutes, from about 2 to 5 minutes, from about 6 to 10 minutes, from about 11 to 15 minutes, from about 16 to 20 minutes, from about 21 to 25 minutes, or from about 26 to 30 minutes. The solvent can be water.

The polymer can be alkyl celluloses, hydroxyalky methylcelluloses, hyaluronic acid, sodium chondroitin sulfate, polyacrylic acid, polyacrylamide, polycyanolacrylates, methyl methacrylate polymers, 2-hydroxyethyl methacrylate polymers, cyclodextrin, polydextrose, dextran, gelatin, polygalacturonic acid, polyvinyl alcohol, polyvinyl pyrrolidone, polyalkylene glycols, or polyethylene oxide. The solvent can be an organic solvent. The polymer can be water-soluble and comprise a polyethylenepolypropylene glycol block copolymer.

The gel transition can occur as a result of in situ cross-linking of the gel composition. The gel composition can comprise cross cationic/anionic cross linkable moieties. The cross linking reaction can be activated by a chemical reaction, a change in temperature, or application of energy. The cross linking can be activated by an application of an energy source selected from the group consisting of radiation, magnetic, ultrasonic, ultra-violet, radio frequency, visible light, and heat.

The composition can undergo a gel transition between about 28° and 41° C. The composition can undergo a gel transition at the physiological pH of a breast milk duct. The pH can be in a range of from about pH 7.5 to about pH 9.0, or in a range of from about pH 7.8 to about pH 8.2. The composition can undergo a gel transition under isotonic conditions.

The gel in the target duct can be distinguishable from tissue. The gel in the target duct can be colored. The gel in the target duct can be harder than tissue. The gel can further comprise an additive to provide detection of the gel inside the target duct. Additionally, an additive may be placed in the gel in order to provide detection of the gel before incision through the breast tissue and skin. The additive can be a dye.

The additive to distinguish the target duct from tissue can be a dye capable of staining ductile tissue with a color visible to the naked eye, a fluorescent dye, a radiographic contrast agent, a radionuclide, a ferromagnetic material, a sonographically reflective material, a thermographically reflective material, an impedance altering molecule, a radioactive agent, a vital dye or an agent detectable by infrared sensor. The additive can be a food coloring dye. The dye can be isosulfan blue, methylene blue, Chicago sky blue, marina blue, tetramethylrhodamine, Texas red-X, or Oregon green. The dye can be a fluorescent dye including, e.g. fluorescein, rhodamine, or indocyanine green. The composition can comprise a therapeutic additive or a diagnostic additive.

The invention further provides a method for forming a in vivo gel map of a breast duct comprising administering to a target breast milk duct a biocompatable composition comprising a polymer in a solvent capable of a gel transition inside the target duct, wherein the composition is liquid at room temperature and undergoes a gel transition inside the target duct within about 30 minutes of delivery of the composition. The method can further comprise cooling any one or more of the target breast, a breast duct access tool, the composition, and the polymer before administering the composition to the target duct. The gel transition time can be in a range from about 0 to 2 minutes, from about 2 to 5 minutes, from about 6 to 10 minutes, from about 11 to 15 minutes, from about 16 to 20 minutes, from about 21 to 25 minutes, or from about 26 to 30 minutes. The composition can be administered using a catheter with a lumen small enough to access a breast milk duct. The lumen of the portion of the catheter that accesses the breast duct comprises a diameter less than 0.10 inches. The composition can further comprise diagnostic or therapeutic additives or additives that aid in detecting the duct.

The invention is a method for identifying one or more breast ducts in a breast or for identifying part of a breast duct for providing a surgeon guidance in a procedure to remove some or all breast tissue from the patient comprising administering to one or more breast ducts in the target breast a biocompatable composition capable of a gel transition inside a breast duct, wherein the presence of the gel inside the duct provides identification of the duct during surgery. The procedure can be for example, a lumpectomy, a partial ductectomy, a total ductectomy, a partial mastectomy, or a total mastectomy.

The invention also provides a kit for mapping a breast milk duct with an in vivo gel comprising a biocompatable composition that is liquid at room temperature and undergoes a gel transition in a breast duct within about 30 minutes of delivery to the target duct, a ductal access tool for delivery of the composition having an access lumen small enough to access a breast milk duct, a container for the kit contents and instructions for use of the kit. The gel transition time can be in a range from about 0 to 2 minutes, from about 2 to 5 minutes, from about 6 to 10 minutes, from about 11 to 15 minutes, from about 16 to 20 minutes, from about 21 to 25 minutes, or from about 26 to 30 minutes.

DESCRIPTION OF THE SPECIFIC EMBODIMENTS

The following preferred embodiments and examples are offered by way of illustration and not by way of limitation.

The invention provides a biocompatable composition comprising a polymer. The composition is useful for partially or completely filling a breast duct with the composition to aide in the surgical excision of a lump in the duct, a part of the duct, the entire duct, a partial mastectomy, or a complete mastectomy. For the composition to be biocompatable, all parts of the composition are biocompatable, thus including the polymer, the solvent and the resulting gel after a gel transition. Any additives must be biocompatable as well. Biocompatability is generally established by government regulatory standards. Compounds that have not been tested against government standards may none the less be biocompatable if they can be tested and approved for use in an animal or human. The biocompatable composition should also be nontoxic, including also that the polymer, solvent, resulting gel and any additives are also nontoxic.

The polymer can be soluble in any solvent, aqueous, organic, non-organic or other solvent, provided the solvent is biocompatable and non-toxic for humans. For the purposes of this invention, the polymer is injected into the ductal lumen and after gelation of the polymer in the duct, the duct is removed by surgical excision. Therefore, the polymer can be optionally biodegradable, although it is not an absolute requirement because most if not all of the gelled polymer is removed upon surgical excision of the breast duct. Where, however, it is anticipated that small amounts of the polymer or gel composition remain behind after such surgical excision, it would be advantageous to the procedure to know that the gel composition left behind will biodegrade within the body within a reasonable period of time.

The solubility of the polymer in the solvent should be greater than 0.5grams per 100 ml of solvent, and thus the polymer in solution can have solubility in a range from about 0.5 grams in 100 ml to, for example, an upper limit of 1 gram per ml. It is understood that the solubility will vary considerably with the addition, or absence of additives, the chemical relationship of the solvent and polymer to each other and other factors (e.g. such as temperature, pH, ion content or concentration, additives, etc.) that affect the gel transition of the polymer in that solvent.

The molecular weight of the polymer molecule should be in a range from about 1 kilodalton to about 500 kilodaltons, thus including such ranges as about 5 kD to about 450 kD, about 10 kD to about 400 kD, about 25 kD to about 350 kD, about 50 kD to about 250 kD, about 75 kD to about 200 kD, and about 100 kD to about 150 kD.

The weight/weight ratio of the polymer to solvent should be in a range between about 0.5:100 to 100:0.5, thus including any such wt/wt ratios of polymer to solvent between a polymer weight of between 0.5 and 100 and a solvent weight of between 100 and 0.5. For example, the polymer weight could be 10 and the solvent weight could be 80, the polymer could be 0.8 and the solvent could be 20, the polymer could be 20 and the solvent could be 10, and so on.

The polymer can be any suitable polymer fitting the specifications listed. Thus, the polymer can include many of the presently known, developed, or otherwise available polymers, copolymers, terpolymers or other polymer-like entities capable of forming a gel under the right conditions for that polymer or polymer composition. For example, any biocompatable polymer listed in THE MERCK INDEX, 12th ed. 1996, Whitehouse Station, N.J. which meets the requirements of the composition as stated can be used.

Some exemplary polymers and the like are disclosed or described in the following publications including, e.g. U.S. Pat. Nos. 5,733,950, 5,739,176, 5,324,519, 5,856,367, 5,702,716, 681,873, 607,686, 5,599,552, 5,502,092, 5,340, 849, 5,278,202, 5,717,030, 5,707,647 and 5,278,201 to Atrix Pharmaceuticals of Fort Collins, Colo.; a product called BioGlue™ produced by CryoLife located at Atlanta, Ga.; cyanoacrylates as described in Trott, J, JAMA 1997 277: 1559–1560; U.S. Pat. Nos. 5,874,500, 5,800,541, 5,783,178, 5,744,545, and 5,739,208 to either Cohesion Technologies of Palo Alto, Calif. or Shearwater Polymers, Inc. of Huntsville, Ala.; U.S. Pat. No. 5,856,367 to Minnesota Mining and Manufacturing Co. of St. Paul, Minn.; U.S. Pat. No. 5,206,341 to Southern Research Institute of Birmingham, Ala.; U.S. Pat. Nos. 5,847,023, 5,593,683 and 5,587,175 to MDV Technologies, Inc. of San Diego, Calif. and FloGel™ product provided by MDV technologies; U.S. Pat. Nos. 5,709,854, and 5,716,404 to Mass. Inst. Tech of Cambridge, Mass.; U.S. Pat. No. 5,630,015 to Ethicon, Inc.

of Somerville, N.J.; U.S. Pat. No. 5,861,174 to University Technology Corp.; U.S. Pat. Nos. 4,100,271 and 4,188,373 to Cooper Laboratories, Inc.; U.S. Pat. No. 5,836,970 to the Kendall Company of Mansfield, Mass.; U.S. Pat. No. 5,660,854 to Haynes et al.; U.S. Pat. No. 4,619,913 to Matrix Pharmaceuticals of Menlo Park, Calif.; WO 97/05185 and WO 96/11671 to Focal Inc. of Lexington, Mass.; WO 97/00275 and WO 96/02276 to Gel Sciences, Inc. of Bedford, Mass.; WO 97/22371 and U.S. Pat. No. 5,475,052 to Collagen Corp. of Palo Alto, Calif.; WO 97/15242 to Seare; WO 96/31547 to Ciba-Geigy; U.S. Pat. No. 5,861,174 to University Technology Corp. of Boulder, Colo.; and U.S. Pat. No. 5,827,835 to Alcon Laboratories of Fort Worth, Tex.

Although the polymer can be any polymer that meets the functional requirements of delivery to a breast duct as described, and composition requirements as stated, the composition can comprise a polymer selected from the group consisting of alkyl celluloses, hydroxyalky methyl celluloses, hyaluronic acid, sodium chondroitin sulfate, polyacrylic acid, polyacrylamide, polycyanolacrylates, methyl methacrylate polymers, 2-hydroxyethyl methacrylate polymers, cyclodextrin, polydextrose, dextran, gelatin, polygalacturonic acid, polyvinyl alcohol, polyvinyl pyrrolidone, polyalkylene glycols, and polyethylene oxide. In addition, the polymer can be water-soluble and comprise a polyethylenepolypropylene glycol block copolymer (see entry number 7722 Poloxamers page 1303, THE MERCK INDEX, 12th ed. 1996, Whitehouse Station, N.J.).

The gel transition of the gel composition in the duct can occur as a result of in situ cross linking of the gel composition. Such a cross linkable gel composition can comprise cross linkable free radicals, or cationic/anionic cross linkable moieties. For example, the gel composition can comprise cyanoacrylates, or FocalGel™. The cross linking reaction can be activated by a chemical reaction, a change in temperature, or the application of energy. The energy source can be light. Indeed, the cross linking can be activated by an application of an energy source selected from the group consisting of radiation, magnetic, ultrasonic, ultra-violet, radio frequency, visible light, and heat. These energy sources can be applied to the polymer or composition just prior to administration in the duct, or can be applied to the breast during or just after the composition is administered to the target duct. The energy sources are derived from standard sources for the energy applied.

The biocompatable composition is liquid before delivery to a breast duct and undergoes a gel transition inside a target breast duct within about 30 minutes of delivery of the composition to the target duct. The gel transition time can be in a range from about 0 to 2 minutes, from about 2 to 5 minutes, from about 6 to 10 minutes, from about 11 to 15 minutes, from about 16 to 20 minutes, from about 21 to 25 minutes, or from about 26 to 30 minutes. The gel may begin to transition slowly, so that a few seconds after the polymer has been exposed to a condition which begins the gelling process, the gelling process can begin, but gelling may not be completed right away. Delivery may be facilitated using the polymer in a liquid form, or a slightly viscous form (i.e., when the gelling is beginning to take place). The gel transition can also begin as soon as about a minute after delivery of the first amount of gel composition to the duct. Preferably the gel transition will not begin until the earliest delivered aliquot of the gel composition has been delivered to and infused to a distal region of the ductal architecture. Alternatively, where delivery is facilitated using a slightly or mildly viscous polymer, the gel transition is beginning sooner than before all or part is delivered to the duct, but the polymer is still of a sufficient consistency that delivery to the duct can be accomplished. Thus, it is preferable that the gel composition undergoes a gel transition after the first-delivered amounts of the composition have had time to infuse through the ductal lumen. A gel composition that gels too soon too completely may block infusion of later-delivered portions of the composition and the duct will not be entirely filled with the gel. The time needed to have the gel composition remain liquid and infuse through the duct will vary depending on such parameters, for example, as the flow rate of the gel composition, the speed of gelation once the gel transition begins, the cause of the gel transition, the depth of penetration of the delivery tool into the catheter, the lumen size of the delivery tool, and the proficiency of the practitioner delivering the gel.

The challenge of delivery of a liquid polymer to a breast duct for a gel transition inside the duct is characterized by among other restrictions the narrowness of the ductal lumen, and the smallness of.the ductal orifice that leads from the nipple surface into the duct, and the extensive relative length of the ductal lumen and the tributary lumens of the ductal architecture that feed into the main lumen. With regard to the ductal orifice size, a catheter having an access tip less than or equal to 0.10 inches may access some of the larger orifices; for smaller orifices catheter tips of 0.050 inches or less are required, and some ductal orifices can only be accessed with tips less than 0.025 inches, and other orifices of the smaller ducts may required an even smaller catheter or entry device lumen, e.g. in the range of from 0.024 to 0.010 inches. Additional challenges include delivering the polymer in liquid form before it gels, and then providing a formulation adapted to conform to a gelation time that appropriates enough time to deliver the gel and which also gels sufficiently quickly to provide a gel structure inside the ductal architecture to identify the duct for excision or other manipulation.

A polymer and solvent mixture (with or without additives that affect gelation, etc.) must be tested for the ability to be delivered to a breast duct in a specific device (i.e. one selected for the procedure) having a certain lumen size, especially where smaller lumen sizes might necessitate such changes in the parameters of the gel composition that facilitate a later gel transition, and higher flow rate of the liquid before gel transition. Delivering the gel composition to suitable animal or other tissue models can test whether a gel composition fits into the parameters required of the composition. Thus, for example, the gel composition can be delivered to rabbit pelts having nipples, pig pelts having nipples, nipples of live rabbits, nipples of live pigs, ducts of mastected human breasts, etc. A simple preliminary non-animal test can be conducted using the gel composition delivered in a catheter to a water bath at an adjusted and appropriate temperature (e.g. at about body temperature or about 37° C.), or the water can be adjusted with other parameters that would be key to the gel transition, for example ion content or pH. Also the bath could be exposed to an activation source, for example a light source in the case where the gel cross links in the presence of visible or other light, as the gel is delivered, or the gel could be delivered to a duct-like tube (e.g. a latex glove finger) resting in the water bath, in order to simulate delivery of the composition to an environment similar to a breast duct either during or prior to activation. Compositions that gel in the bath and not in the catheter would be considered excellent candidates for further tests in animal and human breast milk ducts. See Sukumar et al., (Animal models for breast cancer), *Mutation*

Research. 333(1–2):37–44, 1995 for other examples of suitable animal models for further testing.

Aside from issues of lumen size of the device for delivery of the gel composition to a human breast duct, the device for delivery of the polymer should also be forgiving of breast tissue, and not prone to penetrating or breaking a lumen wall, and not prone to injuring the breast or ductal lumen in any way. Catheters are excellent delivery tools for this purpose because they are not sharp and thus have a reduced risk of rupturing a ductal wall, or nicking tissue. Other delivery devices may also be used, including, e.g. cannulas, needles, other lumens or tubes, especially when these devices are made with forgiving materials and have a forgiving design capable of penetrating a ductal lumen without violating the tissue walls of the lumen.

The delivery tool may penetrate into the ductal lumen as far as necessary for successful delivery of the gel composition. Generally this distance can be in the range from about 1 millimeter to about 5 centimeters, or if practical and necessary, into a location at or beyond the lactiferous sinus. However, it may be the case that a small amount of penetration, e.g. 2 cm may be enough to deliver the liquid gel composition, allowing that the liquid will infuse into the duct on its own once delivered in the top most portion of the ductal lumen. It is anticipated that delivery of the gel composition might begin with a relatively deep insertion of the delivery tool into the ductal lumen, and a subsequent gradual withdrawal of the delivery tool as the liquid is delivered and infused into the duct, and especially as the gel composition begins a gel transition.

A syringe or other infusion device may directly infuse the liquid into the duct, or if attached to the delivery tool, a syringe may infuse the liquid into a delivery lumen of the tool. Delivery of the composition to a breast duct is preferably done by entering the ductal orifice. Preferably during delivery the ductal wall remains intact and the gel material remains within the ductal architecture. The gel composition is injected into the breast duct where it infuses through the ductal architecture that connects with the ductal orifice that was injected. An appropriate preparation for a temperature sensitive polymer in order to provide an appropriate window for administration of the gel and to ensure gelation once inside the duct (and not before) may be cooling the liquid polymer to a temperature below gelation temperature. For example, the polymer may be cooled before it is administered by being placed on ice, or refrigerated. In addition, an administration tool may be cooled, and/or the breast itself may be placed on ice or wrapped in a cooling cloth that lowers the skin temperature. Once administered, the body provides a source of warming and thus allows for gelation. Other measures may be taken for polymers that are not temperature sensitive but which respond to other changes that can be controlled just prior to administration in order to maximize the opportunity for the polymer to penetrate the ductal architecture before gelation occurs. As the liquid polymer is infused into the breast duct, application of external pressure (including e.g. massaging the breast) may be used to encourage a mixing of the liquid with the ductal contents (including ductal fluid), and a diffusion or continued infusion of the liquid into the distal areas of the ductal architecture before substantial gel transition occurs.

The goal of the infusion of liquid polymer is to have the gel composition enter the duct as a liquid and fill the entire duct, including, e.g. the lactiferous sinus, the distal regions of the ductal architecture, and the main lumen of the duct. The liquid polymer must be able to enter the duct and infuse within the duct before it gels (i.e. undergoes a gel transition).

Thus, since it takes a period of time before the liquid has diffused into all regions of the breast duct, or at least the main lumen of the breast duct, the polymer should not undergo a gel transition until it has been substantially infused into at least the lower (most distant) regions of the main ductal lumen. At the point of substantial infusion into the lower regions of the main ductal lumen, and after that where the polymer has filled most of the breast duct, the gel transition can most timely and beneficially occur. Alternatively, the gel can begin to transition early, but slowly, and can complete its transition only after all of the gel or polymer is delivered to the duct. Different gels may act differently with regard to gelation starting time, rate of gelation, time it takes to gel, and final consistency achieved. Many combinations of attributes and qualities of different gel combinations can be worked with to achieve the ultimate goal of creating a map in the duct, and many combinations may be comparatively satisfactory for a given patient scenario.

If too much time passes before the gel transition occurs, the procedure runs the risk of having the solvent diffuse and/or the conditions inside the duct and with the liquid polymer to change to a point that alters any optimal gel transition or the ultimate consistency of the gel. In addition, because the delivery of the gel composition to the breast duct is for the purpose of identifying and then excising the duct in surgery, an optimal time period before the gel transition is complete is approximately a maximum of 30 minutes. Thirty minutes or less allows the anesthetic time to take effect, and the practitioner and assistants time to prepare the surgical site for the procedure. Also, if too much time passes before the gel transition, some of the additives may diffuse into the lumen walls of the duct, and lose their effectiveness for whatever purpose inside the ductal lumen. For example, where an additive is one that can be detected in the gel, and is required to locate the gel-filled duct, if that additive has a chance to diffuse through the lumen wall and perhaps into surrounding tissue before gel transition occurs, the effectiveness of that additive is greatly reduced.

It is estimated that the optimal time period for a gel transition occurring when the liquid polymer is inside the duct is about 30 minutes or less, possibly in a range from about 1 to about 25 minutes, also likely in a range from about 5 to about 20 minutes, credibly in a range from about 8 to about 17 minutes, and also in a range from about 10 to about 15 minutes. Giving the liquid time to enter the duct, requires an approximate 30 seconds to 5 minutes of infusion of the liquid polymer into the duct, during which time the conditions inside the duct are not sufficient to induce a gel transition, and after which time the liquid can be allowed to undergo a gel transition. The gel transition can be virtually immediate, or may take minutes, i.e. up to about 30 minutes altogether from the first moments of infusion of the liquid polymer. Preferably the composition does not begin a gel transition until after it has substantially filled the breast duct, or at least until the earliest delivered portion of the composition has had the opportunity to seep to the deeper recesses of the duct.

Additionally, the gel can harden to various consistencies, provided it becomes less liquid and more viscous once it undergoes a gel transition. Thus, the gel can be, for example, less hard than the surrounding tissue, about the same consistency as the surrounding ductal lumen, somewhat stiffer or harder than the ductal lumen and/or the surrounding breast tissue, or much stiffer and harder than the ductal lumen and/or the surrounding tissue. The main objective is to provide a gel-filled breast duct that is easily identified in virtually its entirety, and which can be excised cleanly leaving clean margins, without rupturing the duct, causing leakage of the gel or ductal contents, and thus containing in the excised material the whole of the sought-after carcinoma or other lesion. The gel hardness may also be considered in more absolute and less comparative terms, so that an essentially viscous gel may work for the purposes of the invention and a much harder gel may also work. To give more or specific detail to hardness or texture of gel, provided is a range of viscosities for various materials that should be sufficient for our hydrogel formulation. The solidified hydrogel can have a viscosity in the range of 1.004 centistokes to −55 Mcentistokes which is similar to the consistency of water to molasses, respectively. For reference, viscosities of other liquids are:

| | |
|---|---|
| Tar | 66M centistokes |
| Honey | 73.6 centistokes |
| Glycerine | 648 centistokes |
| Food oil | 30–32 centistokes |
| Fuel oil | 2–15 centistokes |

The polymer can undergo a gel transition based on a change of conditions inside the breast duct. The conditions changed can be any condition that causes a gel transition for that polymer. Some exemplary and common conditions include e.g. temperature change, pH change and ion change. For example, with regard to temperature, the gel composition can be liquid at temperatures below room temperature (i.e. at temperatures below about 22° to about 27° C.) and can undergo a gel transition in the range of body temperature (i.e. at temperatures in a range from about 35° C. to about 40° C.). In such a case using such temperature sensitive polymers, the polymer can be liquid for example at refrigerated temperatures (i.e. about 2° C. to about 15° C.) and although delivered to a breast duct at room temperature, can be kept on ice or refrigerated until moments before delivery, allowing thus only slight warming before the liquid is delivered to a breast duct. In addition, the delivery tool can be chilled, and the breast can be cooled or wrapped in a cooling pad or contacted with an ice laden water bottle or otherwise chilled or cooled, for example.

Some gel compositions will undergo a gel transition based on a pH change, and thus gel compositions that are liquid at slightly basic or acidic conditions may transition when inside the breast duct having a pH in the range of physiological pH (i.e. in a pH range from about pH 7.2 to about pH 9.2, more specifically in a pH range from about pH 7.5 and pH 9.0, and more specifically in a pH range from about pH 7.8 to about pH 8.2). Generally, body secretions tend to be buffered, and ductal fluid being a body secretion creates a buffered environment inside the breast duct. Thus as a pH sensitive gel composition contacts the somewhat buffered environment of a breast duct containing breast duct fluid it can undergo a gel transition. The pH sensitive composition will be liquid at some non-physiological pH value (being either slightly more acidic or slightly more basic than the physiological pH of a breast duct or breast duct secretions) and will undergo a gel transition inside a breast duct once it contacts the buffered environment of the duct.

Some gel compositions will undergo a gel transition based on ions in the duct. Thus, for example a gel composition that is liquid at hypotonic or hypertonic conditions can undergo a gel transition inside a breast duct that is isotonic. Ionic conditions can be created relative to the ionic condition of breast duct fluid by adding or removing ions relative to the ionic content of ductal fluid from a breast. Such ions can include, e.g. $Na^+$, $Ca^{++}$, $Cl^-$, $Mg^{++}$, $Zn^{++}$, $Fe^{++}$, $K^+$ and other ions that exist in the body in some amounts or which are not harmful to the body. For an indication of the ion content of breast duct fluid see Petrakis et al., "Nipple aspirate fluids in adult nonlactating women—lactose content, cationic $Na^+$, $K^+$, $Na^+/K^+$ ratio, and coloration", Breast Cancer Research & Treatment. 13(1):71–8, 1989.

The biocompatible gel composition in the target duct after gel transition can be distinguishable from tissue, i.e. the surrounding tissue including the ductal lumen and the breast tissue or any cancerous or precancerous tissue in the breast duct. The composition that has undergone its gel transition can be distinguishable by any factor that can distinguish it from tissue, or any number or combination of these factors. The gel might be colorless, for example, but hardened, and by hardening inside the duct, might make the gel and the duct it fills distinguishable from the surrounding breast tissue by virtue of the different density and tensile strength of the gel versus the ductal lumen and surrounding breast tissue. Thus, the stiffness of the duct housing the gel alone can make the duct detectable to a practitioner.

Other mechanisms of making the gel inside the duct distinguishable from tissue include having the gel contain a color different than the surrounding tissue or ductal lumen, and which is visible to the naked eye, or other wise visible with special light. For example, the gel can be pink, green, blue, yellow, purple, or any other color available in a biocompatable dye that can be added to the gel composition before delivery to the duct. Other mechanisms of making the gel distinguishable from the tissue of the breast can include placing additives in the gel that can be detected by nonvisual means. Such nonvisual means can include, e.g. detection by special sensors capable of sensing the particular additive in the gel that is not present in the surrounding tissue. Thus, after the composition has been delivered to the duct and the gel transition has occurred, a gel having such additives can be "read" and detected by using the sensor appropriate for the additive. Thus, for example, a practitioner can begin removal of the target duct and use the sensor to confirm that the right duct is being removed, and that all portions of the target duct are being removed. Tissue that does not read positive with the sensor can be left behind in the breast.

Although it is possible that the biocompatable composition may have very few or no additives, and by virtue of hardening alone can be used to detect the breast duct for surgical excision, it is more likely that at least one if not more than one other additives can be added to the composition to aid in the detection of the gel inside the target duct, and so provide for the detection of the target duct for surgical excision. The additive can provide visual detection of the gel by the naked eye, or can be an additive that is capable of detection by a special sensor or machine or other mechanism that is sensitive to the presence of such an additive and which can detect material that has the additive and distinguish such material from other material not containing the particular additive. Thus, the additive can be, e.g. a food coloring dye, for example a red, blue, green or yellow food coloring dye. For example FD&C green #8, FD&C Blue #1, FD&C Blue #2, FD&C Green #3, FD&C Red #3, FD&C Red #40, FD&C Yellow #5, FD&C Yellow #6 dyes may be used. The additive can also be another type of visually detectable dye including, e.g. isosulfan blue, methylene blue, Chicago sky blue, marina blue, tetramethylrhodamine, Texas red-X, or Oregon green. The additive can be a fluorescent agent, including e.g. any commercially available fluorescent agent that is biocompatible. Some exemplary fluorescent agents include, e.g. fluorescein, rhodamine or indocyanine green, but others also exist and may be available from such companies as Molecular Probes located at Eugene, Oreg., or Promega Corp., located at Madison, Wis., and other companies that supply reagents for biomedical scientific research purposes. Other fluorescent dyes that may be adaptable to use in a gel in a breast duct include green fluorescent protein (GFP) or blue fluorescent protein (BFP).

The additive can also be an agent detectable by other nonvisual means, including, e.g. a radiographic contrast agent, a radionuclide, a ferromagnetic material, a sonographically reflective material, a thermographically reflective material, an impedance altering molecule, a radioactive agent, and an agent detectable by infrared sensor. An agent detectable by infrared sensor is available from HotHands/ Johnston Sales Co., Little Rock, Ark. (phone 501-661-1199). Such agents that are not visually detectable require some kind of sensor or detector to detect their presence. The usefulness of the additives that are detectable by nonvisual means includes that once the duct is removed, the tissue can be passed over with the sensor to determine if all portions of the gel-filled duct have been removed. Where some pieces of gel and/or duct and gel remain, these remnants can also be removed, providing an opportunity of leaving clean margins with little or no risk of reoccurrence of the cancer or precancer that is removed with the ductal excision.

In addition, the additive can be colored so that after delivery to the breast duct it is visible through the skin to aid the practitioner/surgeon to identify the duct externally, and so plan an appropriate location for the initial incision. Such additional quality of a colored gel provides the opportunity to further limit the removal of healthy tissue. Thus the additive can comprise a dye detectable from outside the breast skin before the incision is made.

More than one additive can be used to make the gel-filled duct detectable, each additive perhaps performing a slightly different purpose in the process. For example, an additive that makes the gel visible to the naked eye or to the naked eye with the aide of a special light (e.g. UV light) can be used so that a practitioner can see at a glance where the duct filled with gel is and what kind of cuts need to be made in and around the surrounding tissue to removed the gel-filled duct. However, another additive can also be added in order to detect minute particles of gel in small tributary regions of the duct and to check the tissue area after excision for whether the gel and duct have been completely removed. For example, an additive that can be detected by a sensor, e.g. a radiographic contrast agent, or a radionuclide, can be used and a sensor to detect the radiographic contrast agent or a sensor to detect the radionuclide can be passed over the region of excision to check for complete removal of the target duct and any remaining pieces of gel.

Additives can also be added to the gel composition in order to facilitate specific and differential identification of lump or lesion in a duct. For example, additives that preferentially bind to tumor cell antigens, epitopes, receptors, or other markers could be added to the gel. Such identifiers of tumor or cancer cells could be visible themselves (either aided or unaided with light or other aides or sensors) or could require an additional coupling to a label in order to make the additive identifiable to the practitioner seeking to excise the lump, lesion or other cancerous tissue. Antibodies are one type of additive that may be specific for a tumor cell marker and could also be coupled with a label (such as a florescent tag also provided in the gel) in order that the tumor cells can be visualized by the practitioner seeking to perform the excision. Other additives might include small molecules, antibody fragments, proteins or protein fragments specific for receptors on the tumor cells, or additives that bind molecules associated with the presence of a tumor and which can serve as adequate indicators of the location of a lesion of tumor cells in the duct and the environs of the duct and breast tissue surrounding the duct.

In addition to additives that aid in the detection of the gel in the duct, the composition can have other additives for other purposes. For example, the additive can be therapeutic to the ductal tissue and surrounding tissue. A therapeutic additive can contact the tissue of the ductal lumen and the surrounding breast tissue and act on the lumen or the surrounding tissue, particularly on the tissue that remains behind after the excision to aid in any number of functions including, e.g. healing the tissue from the excision, eliminating any remaining cancerous or precancerous cells in the duct or tissue, antibiotic effects to reduce the risk of infection in the remaining tissue, and any other beneficial therapeutic effects that might be desired after the excision. Thus, such additives can include, e.g. an anticancer or antiproliferative agent, an antibiotic, or a wound-healing agent. Any agent or drug deemed beneficial in locally treating the ductal tissue or surrounding breast tissue during and after the excision of the duct can be added to the gel. In some cases the therapeutic additive may preferentially seep through the gel composition or gel matrix to the ductal lumen and to the surrounding breast tissue to provide its therapeutic benefit.

Agents or drugs that may be used as therapeutic additives for the gel composition include e.g. those discussed and presented in Harris et al. Ed. BREAST DISEASES, J. B. Lippincott Co., Philadelphia, Pa. 1991; Bland and Copeland Ed., THE BREAST, W. B. Saunders Co., Philadelphia, Pa. 1991; and Love, S. THE BREAST BOOK, $2^{nd}$ Ed. Lindsey Ed. Perseus Books, Reading, Mass. 1995. In general any chemotherapeutic agent or hormone modulating agent may be used. For example, such modulators of estrogen activity may provide some protective effect to the surrounding tissue including e.g. tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. The soy isoflavone can be genistein or daidzein. The aromatase inhibitor can be toremifene. Some possible candidate estrogen activity modulators are described in el Khissiin and Leclercq, (1998) *Steroids* 63(11): 565–74; O'Regan et al. (1998) *J Nat'l Cancer Inst* 90(20):1552–8; Favoni and Cupis (1998) *Trends Pharmacol Sci* 19(10): 406–15; Williams, G M (1998) *J Nat'l Cancer Inst* 90:1671; Huynh et al (1996) *Clin Cancer Res* 2:2037–2042; England and Jordan (1997) *Oncol Res* 9:397–402; Ashby et al (1997) *Regul Toxicol Pharmacol* 25:226–31, Long et al., (1998) J Steroid Biochem Mol Biol 67:293–304. In addition, estrogen activity modulators obtained from plants or foods can be used, including soy and soy isoflavones, including genistein and daidzein, as described in Xu et al (1998) *Cancer Epidemiol Biomarkers Prev* 7:1101–8, Charland et al. (1998) *Int J Mol Med* 2:225–228, Franke et al. (1998) *Am J Clin Nutr* 68:1466S–1473S, Kim et al. (1998) *Am J Clin Nutr* 68: 1418S–1425S, Shao et al. (1998) *Cancer Res* 58:4851–7, Shao et al., *Journal of Cellular Biochemistry* 69(1):44–54, 1998; Liggins et al. (1998) *Anal Biochem* 264:1–7, Kinoshita et al. (1998) *Adv Exp Med Biol* 439: 1178–29, and Dees and Kennedy (1998) *Curr Opin Oncol* 10(6):517–522. Estrogen activity modulators that are aromatase inhibitors are described in Mor et al. (1998) *J Steroid Biochem Mol Biol* 67(5–6):403–41 1; Goss et al. (1999) *Oncology* 56(2) :114–121; Coombes (1998) *Recent Results Cancer Res*

152:277–84; Costa et al. (1999) *Cancer* 85:100–3; Long et al. (1998) *J Steroid Biochem Mol Biol* 67(4): 293–304; and Lamb and Adkins (1998) *Drugs* 56(6):1125–40. Gonadotropin hormone releasing agonists (GnRHA) are described at website www.amaassn.org/special/womh/newsline/reuters/03315440.htm (date Apr. 5, 1999); and in other publications including Jonat (1998) *Br J Cancer* 78 Suppl 4:5–8; Szamel et al. (1998) *Cancer Chemother Pharmacol* 42(3):241–6; Ciardo et al. (1998) *Minerva Ginecol* 50(1–2):25–29; Nagy et (1996) *Proc Natl Acad Sci USA* 93(14):7269–73; Burger et al. (1996) *Eur J Obstet Gynecol Reprod Biol* 67(1):27–33.

Additives to the gel composition may also perform a diagnostic function. A diagnostic function may be particularly useful where a lesion is believed to be in the duct, but which has not been specifically located or specifically identified for cell type or by cytology or histology. For example, the gel composition can contain an additive that binds to cell surface proteins on the surfaces of ductal epithelial cells to identify, e.g. abnormal cells. The diagnostic additive can bind soluble factors or molecules that would be detected in the ductal fluid. The diagnostic additive can also be capable of passing through a cell wall and be able to bind intracellular molecules or components. Thus, using a diagnostic additive, the gel-filled duct can be analyzed after excision for the character and contents of the cells and fluid in the duct and on the walls of the lumen. Such analysis can be used subsequently to treat the patient post-excision and/or to monitor the patient for any subsequent occurrence in another breast duct. Preferably the diagnostic agent will be or will be capable of conjugation to a marker agent that will aid in identification of the agent in the duct. For example, the diagnostic agent may be an antibody capable of binding a cell surface marker on a carcinoma cell and will be conjugated to a fluorescent marker that can be identified under fluorescent light. By identifying the location of the diagnostic antibody that preferentially binds the carcinoma cells in the duct, for example, the location of the lesion or lesions in the duct can be identified post excision and/or during the surgical removal of the duct. The cells of the lesion of the excised duct may also be subsequently sampled and further analyzed.

Diagnostic analysis of an excised duct can include examining diagnostic markers in the gel to determine the presence of precancerous or cancerous ductal epithelial cells. The hardened gel in the removed duct can be analyzed for the presence of soluble factors or other components that might indicate the presence of cancerous or precancerous ductal epithelial cells in the duct. The epithelial cells in contact with or trapped within the gel can be analyzed for protein markers, nucleic acid markers, chromosomal abnormalities, or other characteristic changes that would signal the presence of cancerous or precancerous cells. In addition, other cells found in the duct can also be analyzed, e.g. for an increase or decrease in these cells as compared to normal ductal fluid, or for qualities of these cells themselves. Thus, the duct containing the hardened gel can be analyzed e.g. for soluble protein content or presence of other ductal fluid components, including also secreted products of ductal epithelial cells) or the ductal epithelial cells themselves can be analyzed, for example, for cell morphology, for protein markers, for nucleic acid markers, and for biochemical markers. In addition, any of the cells of the duct can be analyzed for morphological abnormalities in cell components, including, e.g. morphological abnormalities of the nucleus, cytoplasm, golgi apparatus or other parts of a cell. The cells can be analyzed for whether they do or don't aggregate (e.g. in clumps) or by making comparisons of the ductal epithelial cells with other cell types retrieved in the ductal fluid (e.g. macrophages, lymphocytes, foam cells and other possible components of ductal fluid). The ductal epithelial cells can be analyzed for their relationship to other (e.g. neighboring or distant) ductal epithelial cells, to other cells in the lumen or surrounding the lumen, (including e.g. myoepithelial cells), and for the molecular contents or the morphology of the ductal epithelial cells, including, e.g. protein markers, nucleic acid markers, biochemical markers in the cells or on the cell surfaces or for any evidence of neoplasia.

In addition to some markers discussed and/or articles or books cited on breast cancer and breast precancer markers, including markers listed in Porter-Jordan and Lippman, "Overview of the biological markers of breast cancer", Hematology/Oncology Clinics of North America vol. 8 (1):73–100, 1994), the following cancer markers are listed here as exemplary and may be used as well as other markers to analyze the condition of a breast duct, including analysis of the ductal contents (including fluid and cells) that are trapped in the hardened gel. Standard assay procedures for identifying the markers can be used, including antibodies or other binding partners, labels, stains, pattern analysis (for cells and cell components), and in general any other chemical or visual identification techniques.

Markers that are presently being studied by researchers presently include, carcinoma embryonic antigen (CEA), prostate specific antigen (PSA) Erb B2 antigen, gross cystic disease fluid protein –15 (GCDFP-15), and lactose dehydrogenase (LDH). For CEA see Imayama et al., *Cancer* 1996, 78(6):1229–34; Inaji et al., *Cancer* 1987,60(12):3008–13; *Mori Int Conger Seer* 1989, 807:211–8; Inaji, et al., *An To Kagaku Ryoho* 1991, 18(2):313–7; Yayoi, et al. *Gan To Kagaku Ryoho* 1994, 21 Suppl 2:133–9; Mori, et al. *Jpn J Clin Oncol* 1989,19(4):373–9; Foretova, et al. *Proc Annu Meet Am Soc Clin Oncol* 1995,14:A101; and Nishiguchi, et al. Rinsho Byori 1992,40(1):67–72. For PSA see Foretova, Garber Lancet 1996,347(9015):1631; Sauter et al., *Cancer Epidemiology, Biomarkers & Prevention.* 5(12):967–70, 1996; Sauter and Daly (1996) *Proc Annu Meet Am Assoc Cancer Res* 37:A1458; and Foretova and Garber (1996) *Proc Annu Meet Am Assoc Cancer Res* 37:A1446. For Erb B2 see Motomura (1995) *Breast Cancer Res and Treat* 33:89–92; and Inaji et al. (1993) *Tumour Biol* 14: 271–8. For GCDFP-15 see Petrakis et al. (1994) *Proc Annu Meet Am Assoc Cancer Res* 35:A1698. For LDH see Mannello et al. (1995) *Cancer* 76:152–4; and Kawamoto (1994) *Cancer* 73:1836–41.

Chromosomal abnormalities in ductal epithelial cells can also provide information and act as a marker to identify cancer or precancer as described in Mark et al. (1999) *Cancer Genet Cytogenet* 108:26–31; Lundlin and Mertens (1998) *Breast Cancer Res Treat* 51:1–15; Newsham (1998) *Am J Pathol* 153:5–9; Larson et al. (1998) *Am J Pathol* 152:1591–8; Adelaide et al. (1998) *Genes Chromosomes Cancer* 22:186–99; Fejzo et al. (1998) *Gene Chromosome Cancer* 22:105–113; Dietrich et al. (1998) *Hum Pathol* 12: 1379–82; Cavalli et al. (1997) *Hereditas* 126:261–8; Adeyinka et al. (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al. (1997) *Ann Clin Lab Sci* 27:47–56; and Fabian et al. 1993 *J. Cellular Biochemistry* 17G: 153–16.

In addition, exemplary markers are described in Masood, (Prediction of recurrence for advanced breast cancer. Traditional and contemporary pathologic and molecular markers) *Surgical Oncology Clinics of North America.* 4(4)

:601–32, 1995; Lopez-Guerrero et al. (1999) *J Hematother* 8(l):53–61; Maijumdar and Diamandis (1999) *Br J Cancer* 79(9–10):1594–602; Balleine et al. (1999) *Br J Cancer* 79 (9–10):1564–71Houston et al. (1999) *Br J Cancer* 79(7–8) :1220–6; Nikolic-Vukosavljevic et al. (1998) *Tumori* 84(6) :691–4; Maguire et al. (1998) *Int J Biol Markers* 13(3) :139–44; Stearns et al. (1998) *Breast Cancer Res Treat* 52(1–3):239–59; Eiriksdottir et al. (1998) *Eur J Cancer* 34(13):2076–81, and U.S. Pat. No. 5,169,774. Many known breast cancer markers are discussed and described in readily available medical textbooks on breast cancer.

The morphology of the cells or cellular contents that are trapped in the duct by the gel may also be examined. The cellular contents can include, e.g. protein, nucleic acid, or other molecular markers in the cells. Cell morphology can serve to establish whether the ductal epithelial cells are normal (i.e. not precancerous or cancerous or having another noncancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma). Analysis of cell contents may serve to establish similar staging as established by morphology, capturing generally a progression of a precancerous or cancerous condition in the cells.

Ductal epithelial cells can be tested for the presence of estrogen receptor for example by any standard technique available for detecting the presence of proteins generally in cells. Some assays provide methods to quantify the results of the tests. Normal cells of the ductal epithelium can be expected to have a high base line of estrogen receptor, i.e. all normal ductal epithelial cells can be expected to stain or register positive for estrogen receptor. Cells that become progressively cancerous, moving from normal to precancerous to cancerous can be expected at some point in that continuum to have more and more ductal epithelial cells that do not have estrogen receptor. Assays for testing for the presence of ER can include standard tests for intracellular receptors. Assays to test for ER presence can also be conducted, e.g. as described in Jacobs et al, (1996) *Eur J Cancer* 32A:2348–53, Pertschuk et al., (1996) *Gynecol Oncol* 63:28–33, Molino et al., (1995) *Breast Cancer Res Treat* 34:221–8, Esteban et al., (1994) *Am J Clin Pathol* 102:158–62, Pertschuk et al., (1994) *J Cell Biochem Suppl* 19:134–7, Poller et al., (1993) *Br. J Cancer* 68:156–61, Chapman et al., (1993) *J Steroid Biochem Mol Biol* 45:367–73, Davies et al., (1 991) *Ann R Coll Surg Engl* 73:361–3, Sklarew et al., (1990) *Cytometry* 359–78, Mobus et al., (1998) *Int J Cancer* (1998) 77(3): 415–23, Mohamood et al., (1997) *J Submicrosc Cytol Pathol* 29(1):1–17, and Jensen, EV, (1996) *Ann NY Acad Sci* 784:1–17. Estrogen receptor immunocytochemistry ER-ICA (available from Abbott laboratories, located in Abbott Park, Ill.) can be used to identify and quantify the ER from a sample of ductal epithelial cells in order to establish an ER positive condition of ductal epithelial cells in the milk duct. The ER-ICA test has been used in FNA procedures to identify estrogen receptors as describe in Azavedo et al, (1986) *Anticancer Research* 6:263–266; Fabian et al. (1997) *J Cell Biochem Suppl* 28–29: 101–110; Flowers et al. (1986) *Ann. Surg.* 203:250–254; McClelland et al., (1987) *Cancer Research* 47: 6118–6122; Sauer et al. (1998) *Anal Quant Cytol Histol* 20(2): 122–126; Tabbara et al. (1998) *Cancer* 84(6): 355–360. Other analysis using estrogen receptors include those described in Masood S., (Prognostic and diagnostic implications of estrogen and progesterone receptor assays in cytology) *Diagnostic Cytopathology* 10(3):263–7, 1994; and Masood et al., (Potential value of estrogen receptor immunocytochemical assay in formalin-fixed breast tumors) *Modern Pathology*. 3(6):724–8, 1990.

For example the gel-filled breast duct can also be used to detect the presence of TGF-β in the ductal fluid trapped by the gel. The ductal fluid and/or ductal epithelial cells contained in the gel can be analyzed for the presence of transforming growth factor-beta (TGF-β). The presence or amount of TGF-β in a fluid or sample is measured against a control, e.g. the presence or amount of TGFβ in a normal sample. Standard ELISA tests (e.g. ELISA tests available from companies providing assays and reagents for molecular biology, e.g. Promega Corporation, located in Madison, Wis.) for TGF-β can be used. Another exemplary means of testing for TGF-β can be polymerase chain reaction (PCR) protocols to test levels of TGF-β mRNA encoding the protein, or other appropriate standard tests for testing protein or transcript levels can also be used. Standard detection assays for proteins or RNA transcripts of genes such as TGF-β are provided by standard protocol books, e.g. in Sambrook, 1989, *Molecular Cloning, A Laboratory Manual*, 2d Ed., Cold Spring Harbor Laboratory Press, Cold Spring Harbor, N.Y., and Ausubel et al., *Current Protocols in Molecular Biology*, 1987–1997 *Current Protocols*, 1994–1997 John Wiley and Sons, Inc. In addition, TGF-β can be tested as described in Li et al., (1998) *J Immunol Methods* 218:85–93 (either bound or unbound from its receptor), Li et al., (1998) *Int J Cancer* 79:455–459, Plath et al. (1997) *J Endocrinol* 155:501–11, Amoils et al. (1996) *Br J Cancer* 73:1255–9, Walker and Gallacher (1995) *J Pathol* 177:123–7, Danielpour and Roberts (1995) *J Immunol Methods* 180:265–71, and Gall et al. (1993) *J Clin Pathol* 46:378–9, Walker and Dearing (1992) *Eur J Cancer* 28: 641–4, and Relf et al. (1 997) *Cancer Res* 57:963–9.

The following are more exemplary potential markers for such diagnosis and analysis or treatment of the gel-filled breast duct. The diagnosis, analysis or treatment can be implemented by placing these diagnostic or therapeutic additives in the composition for delivery to the target breast duct. Exemplary markers or additives can include the following or like molecules with like effects:

cathepsins (including cathepsin D)

maspin, fas, fas ligand, tissue inhibitor of matrix metalloproteinas-1 (TIMP-1)

chemokines (both C—C and C-X-C type chemokines)

collagenases, metalloproteinases, TIMP's, cathepsins, disrupted basement membrane epitopes, stromolysin-3 cytokeratins (e.g. keratin 14, B1, KA1, KA4 and 312C8-1)

estrogen and progesterone receptors (or any androgen or other steroid receptor)

growth factor receptors for members of the fibroblast growth family (FGF) including FGF1-18, vascular endothelial growth factor (VEGF), insulin-like growth factor –1 (IGF-I), IGF-II, platelet-derived growth factor (PDGF), keratinocyte growth factor (KGF), and epithelial growth factor (EGF), placental growth factor (PLGF), hepatocyte growth factor (HGF), tumor necrosis factor (TNF), transforming growth factor (TGF) both alpha and beta forms, and angiopoietin, for example growth factors and cytokines including FGF1-18, VEGF, IGF-I, IGF-II, PDGF, KGF, EGF, PLGF, HGF, TNF, TGF alpha and beta, angiopoietin, for example heat shock proteins (HSP) (e.g. HSP27) 27 (HSP27)

ErB type 1 tyrosine kinase receptors (e.g. Her2 (an EGF receptor) or any ligand or receptor of the ErbB family of ligands and receptors)

integrins, selectins, cadherins, for example (i.e. alpha and beta 3 integrin)

keratin-14 known cancer antigens including, for example Ki-67, Ki-S1, p53, nm23, bcl-2, p21 ras, cyclins, and pS2

Thrombin receptor activating peptide urokinase, urokinase-type plasminogen activator (UPA), plasmin antiplasmin, UPA receptor (UPAR), fibrinogen, plasmin activator inhibitor-1 and 2 (PAI1 and 2)

telomerase antibodies to tumor associated antigen-72 (TAG-72) (e.g. B72.3, B6.2, and TKH2)

carcinoembryonic antigen (CEA)

prostate specific antigen (PSA)

S1 protein alkaline phosphatase myosin sialyl Tn (STn) glycopeptide (e.g. TAG-72)

Tn glycopeptide aneuploidy and/or other chromosomal mutations

The biocompatable gel composition can also be used to make a ductal map of an entire breast where all the ducts are filled in order to aid a surgeon for any procedure involving multiple ducts or a large portion of the breast. In the case where some ducts are filled without intention to excise the duct, the particular biocompatable gel composition useful for mapping the breast ducts (or nearly all the breast ducts) in a given breast are required to be not only biocompatable but also biodegradable, so that after a reasonable period of time (e.g. a few days, a week, a few weeks, or a month or two) the material in the preserved breast ducts biodegrades and the ductal function can return to normal and the lumens of the ducts are essentially cleared of the gel.

In order to use the biocompatable, biodegradable gel composition of the invention, the ducts of the breast can be filled with the liquid composition as described above, with the additional steps that all the ducts (or nearly all the ducts) are accessed and filled with the gel composition. The ducts can be filled at about the same time, or as close to the same time as possible. Thus the ducts can be filled sequentially or essentially simultaneously before the surgical procedure. The gel composition in the breast ducts can undergo a gel transition as described above. The hardened or semi-hardened or viscous gel can be identified by visible color, color detectable with a special light (e.g. UV or fluorescent light) or other detection means in order to guide the surgeon according to the goals of the surgery.

Additives in addition to detection or identification additives may be placed in the gel for mapping the ducts in the breast, including, e.g. therapeutic additives. The therapeutic additives may be, e.g. additives to aid in healing the breast after the breast surgery. The additives may be either retained in the biodegradable gel, or be permitted by the gel matrix and gel transition chemistry to seep from the duct through the ductal wall and into surrounding tissue. In the surrounding tissue, therapeutic additives, e.g. antibiotics, or wound healing additives, may aid the breast tissue to heal after the tissue removable procedure.

The invention provides a process or method for forming an in vivo gel map of a breast duct. The in vivo gel map provides a practitioner/surgeon with a map of a target duct to be excised providing the opportunity to remove the entire duct cleanly, and to leave behind as much benign breast tissue as possible. A gel composition in a duct also can provide an aide to removing a lump in the breast (lumpectomy), removing part of a duct, removing the entire duct (partial or complete ductectomy), or performing a partial or complete mastectomy. In the case of a mastectomy, the gel composition can aid a surgeon to retrieve all or most all parts of the duct or ducts targeted for excision of the breast and thus decrease the likelihood of a reoccurrence of the cancer. Where the additive is a dye or colorant that can be seen through the skin of the breast, a portion of the target duct may be seen from outside the breast after delivery of the composition but before any incision is made in the tissue. The ability to see the location of the duct from outside the breast can aid a surgeon in choosing the site for an initial incision and for devising a surgical plan for removal of the duct in order to preserve as much healthy breast tissue as possible.

The process begins by administering to a target breast duct a biocompatable composition comprising a polymer in a solvent capable of a gel transition inside the target duct. Where multiple ducts are to be excised, or a partial or complete mastectomy is to be performed, multiple ducts are filled with the gel composition. The biocompatable composition can be any such composition, including, e.g. compositions described and cited to herein. The biocompatable composition will comprise a biocompatable polymer and solvent so that the gel composition is a liquid before and during delivery to the target breast duct. Later, once inside the target duct the composition can undergo a gel transition and become a non-liquid gel.

The composition is preferably a liquid at room temperature (i.e. a temperature in a range from about 22° C. to about 27° C.) and undergoes a gel transition once inside the target duct within about 30 minutes of delivery of the composition. Alternatively, the gel transition begins as the composition is delivered and the gel completes the transition some time during or after delivery of the composition to the duct. The gel composition can therefore undergo the gel transition a few minutes after delivery of the first portion of the gel to the target duct. The gel transition can begin e.g. at 0 to 1, or 1 or 2 minutes after delivery is begun of the first portion of the composition to the breast duct, or from about 0 to about 2 minutes, or about 2 to about 5 minutes from delivery of the first portion of the composition to the breast duct, or from about 5 to 10 minutes from delivery of the first portion of the composition to the breast duct, or from about 10 to 20 minutes from delivery of the first portion of the composition to the breast duct, or from about 20 to 30 minutes from delivery of the first portion of the composition to the breast duct. Depending on the final hardness or viscosity of the gel and other parameters or variables such as the lumen size of the delivery tool, the condition change that causes the gel transition, the starting time of gelation, the amount of time it takes for gelation to be complete, the optimal start time and rate can vary and still provide suitable conditions for the method steps.

The composition is administered using a breast duct access tool having a lumen small enough to access a breast milk duct. A catheter may be used as the access tool. The lumen of the access tool may be as large as 0.10 inches in diameter, or in a range from about 0.09 to 0.05 inches in diameter, or in a range from about 0.04 to about 0.025, or in a range from about 0.024 to about 0.010 inches in diameter. The access tool can be any tool capable of accessing a breast milk duct and delivering a gel solution as a liquid. Thus, e.g. the access tool can be a catheter, a cannula, a needle having a lumen, or other lumen containing tool capable of fluid delivery to a breast milk duct.

Access of a breast duct can be facilitated as described in e.g. Love & Barsky, (1996) *Lancet* 348: 997–999, Makita et al. (1991) *Breast Cancer Res Treat* 18: 179–188, or Okazaki et al. (1991) *Jpn J Clin. Oncol.* 21:188–193. Other descriptions of ductal access may be applied to the task of delivering a gel composition, including, e.g. Sartorius et al., "Contrast ductography for recognition and localization of benign and malignant breast lesions: an improved technique" pp. 281–300. In: Logan WW, ed. BREAST CARCINOMA. New York, Wiley, 1977. WV) 870 B8278 1977; Barsky and Love (1996) "Pathological analysis of breast duct endoscoped mastectomies" Laboratory Investigation, *Modern Pathology*, Abstract 67; Lewis (1997) *Biophotonics International*, pages 27–28, May/June 1997; Diner et al (1981) *American J. Radiology* 137: 853; Tabar et al (1983) *Radiology* 149: 31; and Threatt et al. (1987) DUCTOGRAPHY p. 119 Basset and Gold eds, Grune & Stratton, Orlando. A tool such as described in copending and co-owned application U.S. Ser. No. 09/473,510 filed Dec. $27^{th}$, 1999 may also be used for delivery of the composition to the target breast duct. For simultaneous delivery of the composition to multiple ducts, a tool as described in copending and co-owned application U.S. Ser. No. 09/506,477 filed Feb. 29, 2000 can be used.

The principles of access of the duct include that the ductal lumen is accessed through the ductal orifice. A medical tool can be placed in the duct so that its distal tip is just below the ductal orifice. Alternatively the tool can be placed just below the sphincter of the lactiferous sinus, or alternatively further into the duct. The tool may be positioned so that it contacts with fluid in the duct. The tool may also be positioned so that it contacts the lesion in the duct. Thus, the tool can be placed just below the nipple surface, or more distal, e.g. to the lactiferous sinus and beyond. The gel delivery can be facilitated with a medical tool, e.g. a catheter, cannula, shunt, stent or other suitable delivery tool.

The composition used in the process of making the in vivo gel map can have additives that aid in detecting the duct so that the practitioner can find the duct for surgical excision. The composition can also have diagnostic or therapeutic additives as described above.

The invention provides for a kit for mapping a breast milk duct with an in vivo gel (in preparation for surgical excision of the duct, a part of the duct, a lump, or the breast or part of the breast) comprising a biocompatible composition that is liquid at room temperature. The biocompatible composition undergoes a gel transition in a breast duct within 30 minutes of delivery to the target duct. The kit can further comprise a ductal access and delivery tool, e.g. a catheter, stent or shunt, for delivery of the composition to the target breast duct. The tool will have an access lumen small enough to access a breast milk duct, which sizes are described above. The kit also comprises a container for the kit contents and instructions for use of the kit. The instructions for the use of the kit can include instructions on how to store and prepare the biocompatible composition for delivery, how to deliver the composition to the breast duct using a catheter, how to identify the gel-filled breast duct during a procedure including surgical excision of the duct, and how to review the surrounding tissue for whether the duct is excised in its entirety and the margins are clean. Further, where therapeutic or diagnostic additives are present in the composition, how they may be used to treat the wound after surgery or diagnose any lesions in the breast duct can be described in the instructions. The instructions pertaining specifically to the surgery procedures can read very much like the disclosure on page 69 of Goodson W H & King E B, Chapter 4: Discharges and Secretions of the Nipple, The Breast: Comprehensive Management of Benign and Malignant Diseases (1998) 2nd Ed. vol 2, Bland & Kirby eds. W. B. Saunders Co, Philadelphia, Pa. pp. 51–74, or other surgical directive pertaining to a procedure to remove a breast milk duct.

The invention includes a method for identifying one or more breast ducts in a breast for providing a surgeon guidance in a procedure to remove some or all breast tissue from the patient by administering to one or more breast ducts in the target breast a biocompatible composition capable of a gel transition inside a breast duct. During the procedure, the presence of the gel inside the duct provides identification of the duct during surgery. Also, if an additive is present in the composition that is visible from outside the breast, the gel and composition is useful to identify an optimal starting point and pattern for an incision into the breast in order to conserve as much healthy breast tissue as possible. Thus, a method is provided for guiding surgical excision of breast tissue for example where the procedure is a lumpectomy, a partial ductectomy, a total ductectomy, a partial mastectomy, or a total mastectomy.

As described above for forming an in vivo gel map of a target breast duct for surgical excision of the duct, the invention also provides a method of mapping multiple breast ducts (e.g. more than one breast duct, and preferably all or nearly all of the breast ducts in a breast) for identifying more than one breast duct for excision, partial excision, lumpectomy, or for mastectomy (either partial or complete). The invention provides a process for forming an in vivo gel map of the breast ducts in a breast for these and other purposes. The in vivo gel map provides a practitioner/plastic surgeon with a map of the breast ducts so that the ducts are identified and can either be preserved or removed, depending on the surgeon's purpose in identifying the ducts. The process can be conducted much as the process for mapping a target breast duct scheduled for surgical excision by administering to a the breast ducts (e.g. those that can be identified) a biocompatible composition comprising a polymer in a solvent capable of a gel transition inside the ducts. Those ducts that the surgeon intends to preserve are best filled with a gel composition that is also biodegradable.

The biocompatible and biodegradable composition can be any such composition, including, e.g. compositions described and cited to herein. The biocompatible and biodegradable composition will comprise a biocompatible and biodegradable polymer and solvent so that the gel composition is a liquid before and during delivery to the breast ducts. Later, once inside the ducts the composition can undergo a gel transition and become a non-liquid gel, e.g. a viscous or hardened gel.

EXAMPLES

1. Testing Visible Dyes and Other Additives for Affects on Gelatin

The purpose of the experiment was to determine the feasibility of injecting radiopaque material together with hydrogel having various visible dyes into the milk ducts. To determine which dyes can be used alone and in combination with each other with formulations containing hydrogel and radiopaque material for injection into the milk ducts. The visible dyes tested included methylene blue, isosulfan blue, fluorescein, and green food dye. Visualization of the fluorescein was possible with a UV light, and also somewhat by the naked eye.

One duct from each nipple from 2 rabbit pelts (available from Pel-Freez™) and one mature live rabbit (#4923) (available from Kraelik Farms (located in Santa Cruz, Calif.) were catheterized with a 0.011 inches tip Pebax™ catheter and coinjected with 0.1–1 ml of cold (4° C.) hydrogel (Pluronic F-127) in a range of amount from 18% to 20%. The gel contained the radiopaque substance Hexabrix (12–12.7%) with or without the dyes mentioned. Some nipples from live rabbits were cooled prior to injection with bags of ice for 5 minutes or so. After all target nipples were injected, the skin was carefully dissected away from the underlying tissue so that the ducts could be observed. The injected ducts were observed for the extent that the hydrogel could be seen, and the extent to which the duct had been filled. After observation, the ducts were sliced longitudinally and in cross-section with a scalpel to determine the solidity and texture of the hydrogel mixture.

The results of the hydrogel injections indicated that the ducts and apparently at least some of the lobules in one quadrant of each of the injected nipples were filled with colored hydrogel. In some cases the hydrogel probably did not extend all the way to the end of the lobule. The hydrogel formulations that were used remained intact in the ducts even after they were longitudinally cut. Injection of green food color gave the best contrast; isosulfan blue and methylene blue were probably also acceptable. Fluorescein diffused out of the ducts after injection, and may be usable if formulated in a manner that encourages ductal retention of the fluorescein molecules. In addition, in the live animals, the hydrogel flowed further into the ducts in animals where the breast tissue was precooled with ice. See Table I below for details of this experiment for each infusion.

TABLE I

Results of Rabbit Pelt and Live Rabbit Gel Composition Injections

| | Identifier | % Gel | ml | Additives | Tool | Temp | Results |
|---|---|---|---|---|---|---|---|
| 1 | rabbit pelt 1; nipple 1 | 18% F-127 (form A) | 0.4 ml | Hexabrix 12.2%; no dye | Pebax 0.011–0.012 Pebax 0.011–0.012 | 4° C. | gel never solidified |
| 2 | rabbit pelt 1; nipple 2 | 20% F-127 (form B-1) | 0.5 ml | Hexabrix 12.2%; no dye | Pebax 0.011–0.012 Pebax 0.011–0.012 | RT | became solid quickly; resistance to injection at the end of the procedure |
| 3 | rabbit pelt 1; nipple 3 | 20% F-127 (form B-3) | 0.5 ml | Hexabrix 15%; 1% methylene blue; 2% fluorescein | Pebax 0.011–0.012 Pebax 0.011–0.012 | RT | green color noted; good diffusion through the duct |
| 4 | rabbit pelt 1; nipple 4 | 20% F-127 (form B-2) | 0.7 ml | Hexabrix 27%; 1% methylene blue; 2% fluorescein | Pebax 0.011–0.012 Pebax 0.011–0.012 | RT | moderate difficulty in injection; good color/visibility |
| 5 | rabbit pelt 1; nipple 5 | 20% F-127 (form B-3) | 0.9 ml | Hexabrix 15%; 0.06% methylene blue; 0.12% fluorescein | Pebax 0.011–0.012 Pebax 0.011–0.012 | RT | brilliant network of green |
| 6 | rabbit pelt 1; nipple 6 | 20% F-127 (form B) | 0.5 ml | no Hexabrix; 1 drop green food color | Pebax 0.011–0.012 Pebax 0.011–0.012 | RT | see green duct and green ductal lobules and feathery portions of the lobules; color might be more intense with larger dose of dye |
| 7 | live rabbit 4; nipple 1 | 20% F-127 (form B-3) | 0.3 ml | Hexabrix 15%; 1% methylene blue; 2% fluorescein | Pebax 0.011–0.012 Pebax 0.011–0.012 | RT | easy injection - no resistance; at first some flowed out of the nipple; after animal sacrificed similar to nipple 2 below. |
| 8 | live rabbit 4; nipple 2 | 20% F-127 (form B-3) | 0.3 ml | Hexabrix 15%; 0.06% methylene blue; 0.12% fluorescein | Pebax 0.011–0.012 Pebax 0.011–0.012 | on ice | easy injection - no resistance; duct full nearly to ends; after animal sacrificed fluorescein stained tissue outside the duct - dye stained gel inside the duct. |
| 9 | live rabbit 4; nipple 3 | 20% F-127 (form B-2) | 0.3 ml + 0.7 ml | Hexabrix 27%; green food color | Pebax 0.011–0.012 Pebax 0.011–0.012 | on ice | catheter placed inside 5 mm; after 3 ml, put in another 7 ml; after animal sacrificed: duct green - good visual of ductal structure |

TABLE I-continued

Results of Rabbit Pelt and Live Rabbit Gel Composition Injections

| Identifier | % Gel | ml | Additives | Tool | Temp | Results |
|---|---|---|---|---|---|---|
| 10 live rabbit 4; nipple 4 | 18% F-127 (form A) | 0.5 ml | no color; Hexabrix 12.5% | Pebax 0.011–0.012 Pebax 0.011–0.012 | on ice | gel solidified, caught in catheter after catheter popped out of duct |
| 11 live rabbit 4; nipple 5 | 20% F-127 (form B) | 0.5 ml | isosulfan blue (0.65 g) fluorescein (0.85 g) | Pebax 0.011–0.012 Pebax 0.011–0.012 | on ice | catheter popped out after 0.5 ml; gel flowed nicely along duct - color visible from the outside of the animal; after animal sacrificed infection noted in the duct. |

2. Rabbit Duct Detection by Fluoroscopic Hydrogel

The purpose of the experiment was to determine if ducts injected with hydrogel plus radiopaque additive (Hexabrix) alone and also with other dye can be visualized by fluoroscopy. The experiments also aimed to determine the differences in fluoroscopic intensity of injections of different concentrations of the radiopaque compound Hexabrix in formulations of hydrogel.

One rabbit (rabbit 1) from BABCO (located in Berkeley, Calif.) was shaved and placed supine. Nipples one through nine were identified and marked. Using a dissecting microscope to see the ducts, forceps were used to remove keratin plugs at the ductal orifices.

The pre-prepared hydrogel solutions (A, B2, B3) were stored at refrigerated temperatures, and placed on ice until use. The thermosensitive isotonic hydrogel solutions were prepared from Pluronic™ products available from BASF through Sigma Chemicals (located at St. Louis, Mo.), Pluronic F-127 catalogue number P-2443. Basic formulation A contained 20 g of pluronic F-127 polymer and 90 g of phosphate buffered saline (PBS), resulting in an 18% solution. Basic formulation B contained 20 g of pluronic F-127 polymer and 80 g of purified water for a 20% solution. Dyes and contrast agents were added to these basic formulations as follows:

A received 1.5 g Hexabrix contrast agent for a 12 g and 12.5% loading percentage;

B-1 received 1.5 g Hexabrix contrast agent for a 12.3 g and 12.2% loading percentage;

B-2 received 2.74 g Hexabrix contrast agent for a 10.05 g and 27% loading percentage;

B-3 received 1.47 g Hexabrix contrast agent for a 9 g and 15% loading percentage.

The solutions flowed at from 2° C. to 8° C. The solutions formed a stiff hydrogel at 37° C.

Test 1. A 1 cc syringe having a Luer-Lok™ tip was filled with hydrogel solution B-2. A catheter (diameter 0.011 inches) was inserted into a duct. A LuerLok™ syringe was attached to the catheter, and the hydrogel from the syringe was injected into the duct. The gel began gel transition between 30 seconds and 1 minutes after entry into the duct. Pictures were taken of the duct in the breast before surgical cutting. The tissue was separated from the gel-filled duct; the extent of gel spread through the duct was noted; and a cross-section of the duct was made to assess solidity of the gel. The gel-filled duct was excised, and preserved for further analysis. The procedure was repeated for other ducts of each rabbit.

The conclusions drawn from this experiment were that a 27% Hexabrix contrast agent combined with the Pluronic hydrogel could be readily injected and detected by fluoroscopy. The formulation used was able to travel nearly to the ends of the ducts as indicated by the addition of the dye. The contrast agent was visible through a significant part of the ducts but was not always visible in the small distal ends of the ducts even though the hydrogel traveled that far. As indicated by contrast and dye, a thin line of hydrogel is visible going down the nipple, the diameter of which expands considerably towards the end of the injection. Just below the nipple is a collection of hydrogel, presumably in the lactiferous sinus. More distally, the hydrogel is visible fanning out into a thinning ductal network. Table 2 below summarizes the experiment. Conclusions that were drawn from the experiments in Table 2: the slower the injection the more completely the duct was filled; hydrogel was observed to the ends of the ducts; 27% contrast goes to the near ends of the ducts, but was faint.

TABLE 2

Radiopaque Contrast Agent and Visible Dye Additives

| # | identifier | contrast and other dye | comments |
|---|---|---|---|
| 1 | R1- nipple 6- duct1 | from B-2 (27% hexabrix + 20% hydrogel) | injection was easy at first (0.5 cc) and then became difficult |
| 2 | R1- nipple 7 duct 1 | from B-2 (27% hexabrix + 20% hydrogel) | injection had constant resistance |
| 3 | R1- nipple 8 - duct 1 | from B-3 (15% hexabrix + 20% hydrogel) | resistance in delivery; solid hydrogel exited the duct |
| 4 | R1- nipple 5- duct 1 | 10% hydrogel + isosulfan blue and fluoroscein | very faint spot observed around nipple |
| 5 | R1 - nipple 3- duct 1 | from B2 (27% hexabrix + 20% hydrogel) | moderate to heavy resistance, but less resistance at the end - the sinus may have been perforated |
| 6 | R1 - nipple 2- duct 1 | from B3 (15% hexabrix + 20% hydrogel) plus methylene blue & flourescein | resistance moderate to light; spot visible slightly on nipple surface; catheter popped out |

TABLE 2-continued

Radiopaque Contrast Agent and Visible Dye Additives

| # | identifier | contrast and other dye | comments |
|---|---|---|---|
| 7 | R1- nipple 2-duct 2 | from B3 (15% hexabrix + 20% hydrogel) plus methylene blue & flourescein | a tree like ductal structure visible |
| 8 | R1 - nipple 6- duct 2 | from B-2 (27% hexabrix + 20% hydrogel) | injected slowly |
| 9 | R1- nipple 1-duct 1 | from B-2 (27% hexabrix + 20% hydrogel) with food coloring | injected slowly (during 45 seconds); the ducts are visible, but no food color lines them |

Colored Hydrogel Introduced into a Duct of a Mastected Breast

One duct from a mastected human breast was cannulated with a petite catheter and the duct infused with formulation B (20% Pluronic F127) with methylene blue colorant added. The liquid formulation infused easily; in 15 seconds 0.5 cc was infused. The gel solidified promptly. The breast was squeezed and a little bit of the gel escaped at the nipple surface.

4. Hydrogel Formulation Evaluation

The purpose of this experiment was to develop optimal hydrogel formulations and evaluate them in both bench top and animal models. To determine the optimal hydrogel formulation, formulations will be tested mainly for solidification times and solidification temperatures. In addition to characterizing the hydrogels physically, other parameters such as hydrogel travel distance, color contrast, texture, etc. will be examined in an animal model. Some hydrogels will be tested prior to and following autoclaving to determine the effect of this sterilization technique on the hydrogel formulations. The visible dyes tested will be FD&C approved dyes, specifically Blue #1, Yellow #5, and Verdant Green Mx-135 (Pylam Products Company, Inc.; Tempe, Ariz.).

Bench top evaluation of hydrogel formulations involved testing in a water bath system, and measuring parameters such as solidification times and solidification. All hydrogel formulations were made from Pluronic F-127 in the concentration range from 14–15%. Preliminary data on hydrogel formulations developed in the 15–18% range indicate that solidification temperatures were lower than desired; therefore the extensive evaluation of these formulations did not occur at this time. All hydrogel formulations consisted of one of the three visible dyes that were being tested: yellow, blue, or green. Solidification temperature was determined by placing the hydrogels in a water bath at set temperatures in the range of 25–37° C., in increments of 3° C. This range of temperature was chosen to mimic the clinical setting and physiological environment that the hydrogels would experience. After the water bath achieved the desired temperature, the hydrogel was placed in the bath and allowed to incubate for 15 minutes prior to evaluation. Evaluation consisted of visual inspection to determine if the formulation was liquid, viscous, solid, or any other combination of these descriptive factors (i.e. liquid/viscous, viscous/solid, or liquid/solid). Solidification time testing consisted of placing the individual hydrogel formulations in a water bath that is at 37° C. and determining, every minute up to 20–30 minutes, the state of the hydrogel composition. Evaluation, like the solidification temperature, consisted of visual inspection for determination if the formulation was liquid, viscous, and/or solid. It should be noted that testing of most hydrogel compositions occurred pre and post autoclaving to determine the effect this sterilization technique had on all the above mentioned parameters.

Animal testing consisted of evaluation of the above parameters in a live rabbit model. A rabbit was anesthetized and placed in the supine position. The abdomen was shaved to allow exposure of the nipples. One or two ducts from each nipple of a rabbit were catheterized with-a Pebax catheter (tip diameter 0.011"–0.012"). Once the catheter tip was in place, approximately 0.1–1.5 ml of hydrogel was injected into the ductal system. Some nipples were cooled prior to injection of hydrogel with bags of ice for approximately 2 minutes. All hydrogel injected was cooled to 4° C. and in some cases the catheter was cooled prior to and during the delivery process of the hydrogel. In addition, after the hydrogel was administered into the ductal system, some nipples were heated with a lamp in order to facilitate quicker solidification. After all nipples were targeted, the skin was carefully dissected away for visualization of the underlying tissue that contains the ductal system. The injected ducts then could be viewed for evaluation of parameters such as hydrogel travel distance, solidification, etc. Lastly, the ducts were observed for solidification and texture by slicing the ducts both longitudinally and in cross-section. Hydrogel formulations were evaluated after.

The results for the bench top testing as presented in Table 3 display the data solidification times, and solidification temperature and characteristics of the hydrogels. Table 3 reports results for both pre and post-autoclaved hydrogel. Table 4 reports the results of hydrogel formulation evaluated in a live rabbit model. All formulations tested in the rabbit model were post-autoclaved hydrogels.

From bench top testing (Table 3), in general, the higher the percentage of pluronic, the quicker the solidification time and lower the solidification temperature for pre-autoclaved formulations. Majority of the formulations solidified at temperatures that were $\geq 31°$ C. Since internal temperature of the body is approximately 37° C., these formulations meet the physiological characteristics of a hydrogel product. In addition, all formulations were liquid at room temperature which is desired for any formulation for ease of introduction via the catheter into the ductal system (data not indicated in Table 1). Comparing pre-autoclaved formulations to post-autoclaved formulations indicates a shift in solidification temperatures. Most hydrogels reduced solidification temperatures and in doing so, this resulted in an increase in the time to solidify. There does not appear to be correlation between specific color additive and alterations in hydrogel characteristics. Therefore, any of the color dyes that provide the best contrast with surrounding tissue can be utilized in this device.

Table 4 reports results from an animal study. In this table are a series of nipples that were tested on an isolated rabbit with several different hydrogels that were composed of different percentage of hydrogel, and various color dyes. Data reported is introduction time, gelation time, and travel distance. Quantity of hydrogel delivered to each ductal system varied. This was dependent on how much of hydrogel could flow into the duct prior to the gelation process occurring. When hydrogel traveled to the distal portion of the ductal system, approximately 1–2 ml of composition could be introduced. If wheals formed at the base of the nipple, thereby blocking the rest of the ductal system approximately, only 0.5 ml of hydrogel could be introduced. Hydrogel delivery time was $\sim\geq 3$ minutes, this includes times where it was difficult to introduce hydrogel as well. To reduce the amount of delivery time, ice was applied to either the nipple or the syringe or both. By icing the nipple, this kept the hydrogel in a liquid state and made for easier introduction of the hydrogel. Following introduction of hydrogel it took approximately 2–7 minutes for gelation to occur. Longer solidification times could be due to the surrounding tissue being cooled and needed to rise to 37° C. or internal body temperature. In the case where a heat lamp was used, the gelation process was quicker and occurred within one minute. In this experiment, blue dye appeared to provide better contrast with the surrounding tissue than green dye. However, it should be noted that the green dye was faint and could not be seen well. Creating a darker green dye will alleviate the faintness issue and provide another option for hydrogel coloring.

TABLE 3

Pre/Post-Autoclave Hydrogel Formulation Evaluation Bench Top Testing

| Item | % Gel | Date | Solvent | Dye color | Solidification Temp Pre/Post (° C.) | Solidification Time Pre/Post (min) |
|---|---|---|---|---|---|---|
| 1 | 14.5 (B) | 10 May 00 | Water | Blue | 37/34 | 12/10 |
| 2 | 14.5 (G) | 10 May 00 | Water | Green | 37/34 | 12/10 |
| 3 | 14.5 (Y) | 10 May 00 | Water | Yellow | 37/34 | 12/10 |
| 4 | 14.6 (B) | 10 May 00 | Water | Blue | NA/NA | NA/NA |
| 5 | 14.6 (G) | 10 May 00 | Water | Green | NA/NA | NA/NA |
| 6 | 14.6 (Y) | 10 May 00 | Water | Yellow | NA/NA | NA/NA |
| 7 | 14.7 (B) | 10 May 00 | Water | Blue | 31/31 | 3/4 |
| 8 | 14.7 (G) | 10 May 00 | Water | Green | 34/>37 | 5/5 |
| 9 | 14.7 (Y) | 10 May 00 | Water | Yellow | 34/28 | 5/2 |
| 10 | 14.8 (B) | 10 May 00 | Water | Blue | 31/28 | 4/4 |
| 11 | 14.8 (G) | 10 May 00 | Water | Green | 31/34 | 7/17 |
| 12 | 14.8 (Y) | 10 May 00 | Water | Yellow | 31/31 | 7/19 |
| 12 | 14.0 (B) | 06 Apr 00 | Water | Blue | NA/>37 | NA/>15 |
| 13 | 14.0 (G) | 06 Apr 00 | Water | Green | NA/>37 | NA/>15 |
| 14 | 14.2 (B) | 06 Apr 00 | Water | Blue | NA/>37 | NA/>15 |
| 15 | 14.2 (G) | 06 Apr 00 | Water | Green | NA/>37 | NA/>15 |
| 16 | 14.4 (B) | 06 Apr 00 | Water | Blue | NA/37 | NA/12 |
| 17 | 14.4 (G) | 06 Apr 00 | Water | Green | NA/>37 | NA/12 |
| 18 | 14.6 (B) | 06 Apr 00 | Water | Blue | NA/31 | NA/4 |
| 19 | 14.6 (G) | 06 Apr 00 | Water | Green | NA/31 | NA/4 |
| 20 | 14.8 (B) | 06 Apr 00 | Water | Blue | NA/31 | NA/4 |
| 21 | 14.8 (G) | 06 Apr 00 | Water | Green | NA/31 | NA/4 |
| 22 | 15.0 (B) | 06 Apr 00 | Water | Blue | NA/31 | NA/3 |
| 23 | 15.0 (G) | 06 Apr 00 | Water | Green | NA/31 | NA/4 |
| 24 | 14.0 (B) | 06 Apr 00 | PBS | Blue | NA/>37 | NA/>15 |
| 25 | 14.0 (G) | 06 Apr 00 | PBS | Green | NA/>37 | NA/>15 |
| 26 | 14.2 (B) | 06 Apr 00 | PBS | Blue | NA/>37 | NA/>15 |
| 27 | 14.2 (G) | 06 Apr 00 | PBS | Green | NA/>37 | NA/>15 |
| 28 | 14.4 (B) | 06 Apr 00 | PBS | Blue | NA/>37 | NA/>15 |
| 29 | 14.4 (G) | 06 Apr 00 | PBS | Green | NA/>37 | NA/>15 |
| 30 | 14.6 (B) | 06 Apr 00 | PBS | Blue | NA/31 | NA/>15 |
| 31 | 14.6 (G) | 06 Apr 00 | PBS | Green | NA/31 | NA/4 |
| 32 | 14.8 (B) | 06 Apr 00 | PBS | Blue | NA/31 | NA/3 |
| 33 | 14.8 (G) | 06 Apr 00 | PBS | Green | NA/31 | NA/5 |
| 34 | 15.0 (B) | 06 Apr 00 | PBS | Blue | NA/25 | NA/2 |
| 35 | 15.0 (G) | 06 Apr 00 | PBS | Green | NA/25 | NA/2 |

TABLE 4

Pre/Post Autoclaved Hydrogel Evaluation Live Rabbit Model

| Nipple No. | Form. | Introduction Time (min) | Volume (ml) | Gelation Time (min) | Travel Distance | Comments |
|---|---|---|---|---|---|---|
| 1 | Nipple not used. | — | — | — | — | — |
| 2 | 14.8(B) H₂O (6 Apr 00) | 1.5–2 | 1–1.5 | ~5 | End of ductal system | Blue very good contrast color. Difficult at first. Iced nipple and syringe and flow became easier. |
| 3 | 14.6(G) H₂O (6 Apr 00) | 2 | .7 | ~6 | Not to ends of system. Wheal at base of nipple, | No icing of nipple. |
|  | 14.6(B) H₂O (6 Apr 00) | 1–2 | .6 | ~7 | Not to ends of system. Wheal at base of nipple, | No ice. |
| 4 | 15.0(B) H₂O (6 Apr 00) | 2.5–3 | .5 | ~1 | Wheal at base of nipple | Iced nipple for easier flow. Used heat lamp to gel quicker |
| 5 | Nipple not used | — | — | — | — | — |
| 6 | Nipple not used | — | — | — | — | — |
| 7 | 14.8(G) H₂O (6 Apr 00) | 2 | 1.5–2.0 | ~2 | End of ductal system | Difficult at first, needed to ice nipple and syringe. Green color too light. Darker would be better. |
| 8 | 14.8(B) PBS (6 Apr 00) | NA | 1.2 | ~2–3 | Wheal at base of nipple. Travel to some portion of distal duct | Easy to inject. Needed to ice nipple and syringe |
|  | 14.8(G) PBS (6 Apr 00) | NA | 1.4 | ~2–3 | Wheal at base of nipple. Travel to some portion of distal duct | Easy to inject. Needed to ice nipple and syringe. Green somewhat difficult to see, darker green would be better. |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for forming a in vivo gel map of a breast duct comprising:
   administering to a target breast milk duct a biocompatable composition comprising a polymer in a solvent capable of a gel transition inside the target duct,
   wherein the composition is liquid at room temperature and undergoes a gel transition inside the target duct within about 30 minutes of delivery of the composition.

2. A method as in claim 1, further comprising cooling any one or more of the target breast, a breast duct access tool, the composition, and the polymer before administering the composition to the target duct.

3. A method as in claim 1, wherein the gel is selected to have a transition time from the group of transition time ranges consisting of from about 0 to 2 minutes, from about 2 to 5 minutes, from about 6 to 10 minutes, from about 11 to 15 minutes, from about 16 to 20 minutes, from about 21 to 25 minutes, and from about 26 to 30 minutes.

4. A method as in claim 1, wherein the composition is administered using a catheter with a lumen small enough to access a breast milk duct.

5. A method as in claim 1, wherein the lumen of the portion of the catheter that accesses the breast duct comprises a diameter less than 0.10 inches.

6. A method as in claim 1, wherein the composition further comprises diagnostic or therapeutic additives or additives that aid in detecting the duct.

7. A method for identifying one or more breast ducts in a breast or for identifying part of a breast duct for providing a surgeon guidance in a procedure to remove some or all breast tissue from the patient comprising:
   administering to one or more breast ducts in the target breast a biocompatable composition capable of a gel transition inside a breast duct, wherein the presence of the gel inside the duct provides identification of the duct during surgery.

8. A method as in claim 7, wherein the procedure is selected from the group consisting of a lumpectomy, a partial ductectomy, a total ductectomy, a partial mastectomy, and a total mastectomy.

9. A kit for mapping a breast milk duct with an in vivo gel comprising a biocompatable composition that is liquid at room temperature and undergoes a gel transition in a breast duct within about 30 minutes of delivery to the target duct, a ductal access tool for delivery of the composition having an access lumen small enough to access a breast milk duct, a container for the kit contents and instructions for use of the kit.

10. A kit as in claim 9, wherein the gel transition time is selected from the group of ranges consisting of from about 0 to 2 minutes, from about 2 to 5minutes, from about 6 to 10 minutes, from about 11 to 15 minutes, from about 16 to 20 minutes, from about 21 to 25 minutes, and from about 26 to 30 minutes.

* * * * *

UNITED STATES PATENT AND TRADEMARK OFFICE
CERTIFICATE OF CORRECTION

PATENT NO. : 6,589,998 B1
DATED : July 8, 2003
INVENTOR(S) : Annette Bianchi et al.

It is certified that error appears in the above-identified patent and that said Letters Patent is hereby corrected as shown below:

<u>Title page,</u>
Item [75], Inventors, replace "Cedarburg, WI (US)" with -- Mountain View, CA (US) --

<u>Column 29,</u>
Line 13, replace "in vivo" with -- *in vivo* --.

<u>Column 30,</u>
Line 19, replace "in vivo" with -- *in vivo* --.

Signed and Sealed this

Twenty-seventh Day of January, 2004

JON W. DUDAS
*Acting Director of the United States Patent and Trademark Office*